US011017903B2

(12) United States Patent
Wan et al.

(10) Patent No.: US 11,017,903 B2
(45) Date of Patent: May 25, 2021

(54) HEART FAILURE READMISSION EVALUATION AND PREVENTION SYSTEMS AND METHODS

(71) Applicant: University of Central Florida Research Foundation, Inc., Orlando, FL (US)

(72) Inventors: Thomas T. h. Wan, Chuluota, FL (US); Varadraj Gurupur, Oviedo, FL (US)

(73) Assignee: University of Central Florida Research Foundation, Inc., Orlando, FL (US)

(*) Notice: Subject to any disclaimer, the term of this patent is extended or adjusted under 35 U.S.C. 154(b) by 121 days.

(21) Appl. No.: 15/976,274

(22) Filed: May 10, 2018

(65) Prior Publication Data
US 2018/0330826 A1    Nov. 15, 2018

Related U.S. Application Data

(60) Provisional application No. 62/505,620, filed on May 12, 2017.

(51) Int. Cl.
*G16H 50/30* (2018.01)
*G16H 50/70* (2018.01)
(Continued)

(52) U.S. Cl.
CPC ........... *G16H 50/30* (2018.01); *G16H 20/60* (2018.01); *G16H 20/70* (2018.01); *G16H 40/60* (2018.01);
(Continued)

(58) Field of Classification Search
CPC ........ G16H 10/60; G16H 40/63; G16H 50/20; G16H 50/30; G16H 50/70; G06F 19/00; G06Q 50/22
See application file for complete search history.

(56) References Cited

U.S. PATENT DOCUMENTS 7,853,456 B2 * 12/2010 Soto ............... G06Q 40/08 705/2
8,751,257 B2 * 6/2014 Amland ............ G06Q 50/22 705/2

(Continued)

OTHER PUBLICATIONS

Ayoub, Ramez. "Decision Support for Reducing 30-Day Readmissions: General Medicine Patients in Community Hospitals." Nov. 24, 2013. Purdue University, thesis. pp. vii, 43-59, 67-78. (Year: 2013).*

(Continued)

*Primary Examiner* — Janice A Mooneyham
*Assistant Examiner* — Chance L Smith
(74) *Attorney, Agent, or Firm* — Locke Lord LLP; Daniel J. Fiorello

(57) ABSTRACT

A method of treating a patient to prevent heart failure readmission can include identifying one or more risk factors for the patient, and selecting one or more interventions relating to the one or more risk factors in a graphical user interface (GUI) of a treatment support system. The method also includes receiving a statistical score of the one or more interventions to determine the effect of the one or more selected interventions on heart failure readmission, and treating the patient as a function of the received statistical score using the one or more interventions.

20 Claims, 9 Drawing Sheets

(51) Int. Cl.
*G16H 50/20* (2018.01)
*G16H 20/60* (2018.01)
*G16H 20/70* (2018.01)
*G16H 40/60* (2018.01)
*G16H 10/60* (2018.01)

(52) U.S. Cl.
CPC ............. *G16H 50/20* (2018.01); *G16H 50/70* (2018.01); *G16H 10/60* (2018.01)

(56) References Cited

U.S. PATENT DOCUMENTS

| | | | | |
|---|---|---|---|---|
| 9,805,163 | B1* | 10/2017 | Panch | G06F 19/325 |
| 2005/0216312 | A1* | 9/2005 | Bellin | G06Q 10/10 |
| | | | | 705/3 |
| 2013/0212508 | A1* | 8/2013 | Barsoum | G06Q 10/10 |
| | | | | 715/771 |
| 2014/0200915 | A1* | 7/2014 | Ryan | G06Q 10/10 |
| | | | | 705/2 |
| 2014/0350957 | A1* | 11/2014 | Calo | G16H 10/60 |
| | | | | 705/2 |
| 2014/0350967 | A1* | 11/2014 | Geleijnse | G16H 50/50 |
| | | | | 705/3 |
| 2014/0379363 | A1* | 12/2014 | Hart | G06F 19/3431 |
| | | | | 705/2 |
| 2015/0261924 | A1* | 9/2015 | Geleijnse | G06Q 50/01 |
| | | | | 705/2 |
| 2018/0374581 | A1* | 12/2018 | Berringer | G06F 19/00 |

OTHER PUBLICATIONS

Dai, Shengchuan. "Kansas City Cardiomyopathy Questionnaire Utility in Prediction of 30-Day Readmission Rate in Patients with Chronic Heart Failure." Hindawi Publishing Corporation. May 23, 2016. pp. 2-5. (Year: 2016).*

"Hypthesis Testing for Means & Proportions." Website. http://sphweb.bunnc.bu.edu/otlt/MPH-Modules/BS/BS704_HypothesisTest-Means-Proportions/BS704 HypothesisTest-Means-Proportions_print.html. 2015. (Year: 2015).*

K. Rav-Marathe et al., "A Systematic Review on the KAP-O Framework for Diabetes Education and Research", Medical Research Archives, vol. 3 issue 9, KEI Journals 2016.

K. Rav-Marathe et al., "The Effect of Health Education on Clinical and Self-Reported Outcomes of Diabetes in a Medical Practice", Journal of Integrated Design and Process Science, Transactions of the SDPS, 20 (1), 2016, 45-63.

T. T H Wan, et al., "KMAP-O Framework for Care management Research of Patients with Type 2 Diabetes", World Journal of Diabetes, Baishideng Publishing Group Inc., vol. 8 No. 4, Apr. 15, 2017, 165-171.

* cited by examiner

HEART FAILURE READMISSION EVALUATION AND PREVENTION SYSTEMS AND METHODS

CROSS-REFERENCE TO RELATED APPLICATIONS

This application claims priority to and the benefit of U.S. Provisional Application No. 62/505,620, filed May 12, 2017, the entire contents of which are herein incorporated by reference in their entirety.

BACKGROUND

1. Field

The present disclosure relates to health care, more specifically to systems relating to heart failure readmission evaluation and prevention.

2. Description of Related Art

Human factors play an important role in health care outcomes of heart failure patients. Traditionally, there has been no way to quantify such factors for use in reducing heart failure readmission. Such conventional methods and systems have generally been considered satisfactory for their intended purpose. However, there is still a need in the art for improved health care systems. The present disclosure provides a solution for this need.

SUMMARY

A method of treating a patient to prevent heart failure readmission can include identifying one or more risk factors for the patient, and selecting one or more interventions relating to the one or more risk factors in a graphical user interface (GUI) of a treatment support system. The method also includes receiving a statistical score of the one or more interventions to determine the effect of the one or more selected interventions on heart failure readmission, and treating the patient as a function of the received statistical score using the one or more interventions.

The one or more interventions can include at least one of rest intervention, environment intervention, nutrition intervention, activity intervention, home visit intervention, technology intervention, interpersonal relationship intervention, or patient psychological intervention, or any combination thereof. Patient psychological intervention can include at least one of patient choice intervention, trust intervention, or patient outlook intervention, or any combination thereof.

Receiving the statistical score can include receiving at least one of a significance value, a beta value, or odds ratio of avoiding readmission compared to treatment without the one or more interventions. In certain embodiments, all of the above can be received simultaneously.

In accordance with at least one aspect of this disclosure, a treatment support system for preventing readmission due to heart failure can include a database comprising a plurality of readmission prevention statistical scores for a plurality of interventions and/or one or more combinations thereof, and a graphical user interface (GUI) operatively connected to the database and including a plurality of intervention buttons which each display a corresponding intervention or combination of interventions. The intervention buttons can be configured to allow a clinician to select one or more interventions by clicking the one or more intervention buttons. The GUI can be configured to display a statistical score for the selected one or more interventions to allow the clinician to treat a patient as a function of the provided statistical score.

The one or more interventions includes at least one of rest intervention, environment intervention, nutrition intervention, activity intervention, home visit intervention, technology intervention, interpersonal relationship intervention, or patient psychological intervention, or any combination thereof. In certain embodiments, patient psychological intervention includes at least one of patient choice intervention, trust intervention, or patient outlook intervention, or any combination thereof.

Displaying the statistical score can include displaying at least one of a significance value, a beta value, or odds ratio of avoiding readmission compared to treatment without the one or more interventions. In certain embodiments, displaying the statistical score can include displaying all of the significance value, the beta value, and the odds ratio of avoiding readmission compared to treatment without the one or more interventions.

The GUI can include a single intervention model pane which includes only single intervention buttons that each display a single intervention and that cause the display of a statistical score of a single intervention that is selected. In certain embodiments, the GUI can additionally or alternatively include an additive intervention model pane which includes combination intervention buttons that each display combination interventions and that cause the display of a statistical score of a combination intervention that is selected.

In certain embodiments, the combination intervention buttons can include a Choice*Interpersonal Relationships*Nutrition button for displaying a statistical score from the database for the combination of patient choice intervention, interpersonal relationship intervention, and nutrition intervention. In certain embodiments, the combination intervention buttons can include a Choice*Outlook*Nutrition button for displaying a statistical score from the database for the combination of patient choice intervention, patient outlook intervention, and nutrition intervention.

In accordance with at least one aspect of this disclosure, a non-transitory computer readable medium includes computer readable instructions configured to cause a computer to perform a method. The method includes displaying a graphical user interface (GUI) including a plurality of intervention buttons which each display a corresponding intervention or combination of interventions, the intervention buttons configured to allow a clinician to select one or more interventions by clicking the one or more intervention buttons, receiving a selection of an intervention button corresponding to the one or more interventions from the user, looking up a statistical score in a database of the intervention or combination of interventions that corresponds to the selected intervention button, and displaying the statistical score in the GUI for the selected intervention or combination of interventions to allow the clinician to treat a patient as a function of the provided statistical score. The one or more interventions can be as described above, for example.

Displaying the statistical score can include displaying at least one of a significance value, a beta value, or odds ratio of avoiding readmission compared to treatment without the one or more interventions. In certain embodiments, displaying the statistical score includes displaying all of the significance value, the beta value, and the odds ratio of avoiding readmission compared to treatment without the one or more interventions.

Displaying the GUI can include displaying a single intervention model pane which includes only single intervention buttons that each display a single intervention, wherein displaying the statistical score includes displaying a statistical score of a single intervention that is selected. Displaying the GUI can include displaying an additive intervention model pane which includes combination intervention buttons that each display combination interventions, wherein displaying the statistical score includes displaying of a statistical score of a combination intervention that is selected.

These and other features of the systems and methods of the subject disclosure will become more readily apparent to those skilled in the art from the following detailed description taken in conjunction with the drawings.

BRIEF DESCRIPTION OF THE DRAWINGS

So that those skilled in the art to which the subject disclosure appertains will readily understand how to make and use the devices and methods of the subject disclosure without undue experimentation, embodiments thereof will be described in detail herein below with reference to certain figures, wherein.

DETAILED DESCRIPTION

Figure 1:
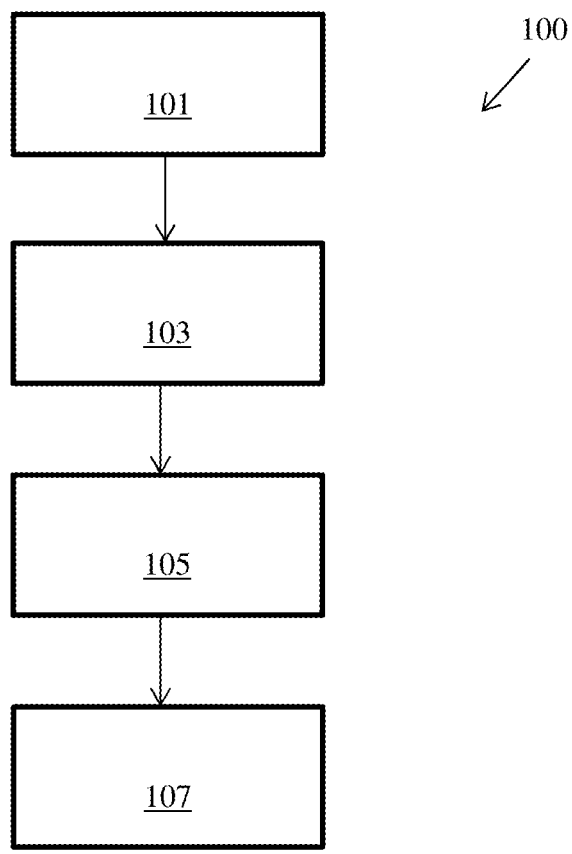
FIG. 1 is a flow diagram of an embodiment of a method in accordance with this disclosure.

Reference will now be made to the drawings wherein like reference numerals identify similar structural features or aspects of the subject disclosure. For purposes of explanation and illustration, and not limitation, an illustrative view of an embodiment of a method in accordance with the disclosure is shown in FIG. 1 and is designated generally by reference character 100. Other embodiments and/or aspects of this disclosure are shown in FIGS. 2-4B.

Based on the systematic review of the scientific studies reviewed by the research team, meta analysis of human factors influencing the relative risk of avoiding the hospital readmission rate for heart failure was performed. Logistic regression with multiple risk factors for heart failure was performed, using a database created for the meta analysis.

The methodology includes a main effects model, also referred to as a single intervention model. The statistically significant level at 0.05 was used and guided by the selection of the variables with a backward selection procedure (put all independent variables into the model and then delete the one with biggest p value, then rerun the model with the same selection criteria until all the independent variables in the model are significant).

TABLE 1

| Principles/Significant | 1 | 0 | Sig. Variable |
|---|---|---|---|
| Choice | 102 | 13 | |
| Rest | 3 | 112 | * |
| Environment | 0 | 115 | |
| Activity | 44 | 71 | |
| Trust | 0 | 115 | |
| Interpersonal | 24 | 91 | ** |
| Outlook | 18 | 97 | ** |
| Nutrition | 68 | 47 | |

Note:
** p value < 0.0001 and
* p value < 0.05

In accordance with the above, the Hypothesized Main Effects Model can be:

significant (event='1')=Rest Interpersonal Outlook (1)

Since the P-value=0.59 is larger than the significance level a=0.05, we fail to reject the null hypothesis. Therefore, there is not enough evidence at a=0.05 level to conclude that there is lack of linear fit.

The methodology can include an interaction effects model (e.g., also referred to as a combination intervention model). The interaction effect can be added into the logistic model (significant (event='1')=intervention) each time to see whether it is statistically significant or not.

TABLE 2

| Interactions | P-Value | Significant |
|---|---|---|
| Activity*Choice | 0.03 | *__ |
| Activity*Outlook | | **__ |
| Choice*Nutrition | 0.25 | |
| Choice*Outlook | | **__ |
| Rest*Outlook | 0.71 | |
| Outlook*Interpersonal | | **__ |
| Activity*Choice*Nutrition | 0.012 | *__ |
| Choice*Interpersonal*Nutrition | 0.0008 | *__ |
| Choice*Interpersonal*Outlook | | **__ |
| Choice*Nutrition*Outlook | | **__ |
| Activity*Choice*Interpersonal*Nutrition | | **__ |
| Activity*Choice*Rest*Nutrition | 0.71 | |
| Activity*Choice*Interpersonal*Nutrition*Outlook | | **__ |
| Activity*Choice*Interpersonal*Nutrition*Outlook*Rest | 0.98 | |

Then, all statistically significant interaction terms were added into the main effects model (1) and use the backward selection to select the variables. The following is the final model with all statistically significant variables:
sig(event='1')=
Rest Interpersonal Outlook Activity*Outlook
Activity*Choice*Nutrition
Choice*Interpersonal*nutrition
Choice*Nutrition*outlook

TABLE 3

Analysis of Maximum Likelihood Estimates

| Parameter | DF | | | Estimate | Standard Error | Wald Chi-Square | Pr > ChiSq |
|---|---|---|---|---|---|---|---|
| Intercept | | | 1 | 0.7958 | 0.0985 | 65.2970 | <.0001 |
| Rest | 1 | | 1 | 2.5609 | 0.5841 | 19.2242 | <.0001 |
| Interpersonal | 1 | | 1 | −1.3838 | 0.2586 | 28.6308 | <.0001 |
| Outlook | 1 | | 1 | −2.8529 | 0.5093 | 31.3815 | <.0001 |
| Activity*Outlook | 1 | 1 | 1 | −2.0542 | 0.7421 | 7.6617 | 0.0056 |
| Choice*Activi*Nutrit | 1 | 1 | 1 | −0.5258 | 0.1723 | 9.3084 | 0.0023 |
| Choice*Interp*Nutrit | 1 | 1 | 1 | 1.9551 | 0.4310 | 20.5818 | <.0001 |
| Choice*Outloo*Nutrit | 1 | 1 | 1 | 1.4500 | 06515 | 4.9536 | 0.0260 |

TABLE 4

Odds Ratio Estimates

| Effect | Point Estimate | 95% Wald Confidence Limits | |
|---|---|---|---|
| Rest 1 vs 0 | 12.948 | 4.121 | 40.680 |
| Interpersonal 1 vs 0 | 0.251 | 0.151 | 0.416 |
| Outlook 1 vs 0 | 0.058 | 0.021 | 0.156 |
| AO 1 vs 0 | 0.128 | 0.030 | 0.549 |
| ACN 1 vs 0 | 0.591 | 0.422 | 0.829 |
| CIN 1 vs 0 | 7.065 | 3.036 | 16.441 |
| CNO 1 vs 0 | 4.263 | 1.189 | 15.284 |

As shown in table 4, odds of reducing heart failure readmission with rest intervention is about 13 times more than that without rest intervention. For interactions, the odds of reducing heart failure readmission with Choice*Interpersonal Relationships*Nutrition and Choice*Outlook*Nutrition are about 7 and 4 times more than that without those, respectively.

TABLE 5

Hosmer and Lemeshow Goodness-of-Fit Test

| Chi-Square | DF | Pr > ChiSq |
|---|---|---|
| 2.1001 | 5 | 0.8351 |

As shown in Table 5, since the P-value=0.835 is larger than the significance level a=0.05, we fail to reject the null hypothesis. Therefore, there is not enough evidence at a=0.05 level to conclude that there is lack of linear fit.

From the final model, it can confidently be said that the "Rest Intervention" can significantly reduce the heart failure readmission and the odds of reducing heart failure readmission with such an intervention is about 13 times more than that without a rest intervention. However, "Interpersonal Relationships" and "Outlook" Interventions have no significant reduction on heart failure readmission. Although there is little evidence to say that "Choice" and "Nutrition" are significant on heart failure readmission respectively, both the combinations of Choice* Interpersonal Relationships*Nutrition intervention and Choice*Outlook*Nutrition intervention can significantly reduce heart failure readmission. For example, the odds of reducing heart failure readmission with Choice*Interpersonal Relationships*Nutrition intervention is about 7 times more than that without it, while the odds of reducing heart failure readmission with Choice*Outlook*Nutrition intervention is about 4 times more than that without it.

Embodiments identify the significance of human factors that affect hospital readmissions for patients suffering from heart failure. Embodiments use Structural Equation Modeling and meta analysis to obtain the desired results. The results identify the associated probability value for the individual factors such as self-efficacy, activity, nutrition, habits, homecare, patient-physician communication and other important personal factors that lead to reduction of re-hospitalization. Embodiments allow a physician to learn how the eight guiding principles of choice, rest, environment, activity, trust, interpersonal relationships, outlook, and nutrition reduce heart failure (HF) readmissions, and to treat a patient accordingly.

Appropriate keywords were identified related to the (1) independent variable of hospitalization and treatment, (2) the moderating variable of care management principles, (3) the dependent variable of readmission, and (4) the disease of heart failure to conduct searches in nine databases. Databases searched included CINAHL, Cochrane Central Register of Controlled Trials, Cochrane Database of Systematic Reviews, ERIC, MedLine, PubMed, PsycInfo, Science Direct, and Web of Science. Only prospective studies associated with heart failure hospitalization and readmissions, published in English, Chinese, Spanish, and German journals between Jan. 1, 1990 and Aug. 31, 2015 were included for the above data systematic review. In the meta-analysis, data was collected from studies that measured heart failure readmission for individual patients. The results indicate that an intervention involving human factor principles may nearly double an individual's probability of not being readmitted. Participants in interventions that incorporated single or combined principles were 1.4 to 6.8 times less likely to be readmitted, for example.

Therefore, interventions with human factor principles reduce readmissions among heart failure patients can be designed to reduce the risk for readmissions. A patient decision support system, e.g., a system as described herein, can allow for a risk reduction approach to be utilized by a physician to reduce readmission rates.

Independent and combined effects of Education and Assessment are the most beneficial strategies. Exercise combined with Education and Assessment or Rest and Relaxation shows greater benefits than Exercise alone. Nutrition combined with other intervention components reveals a clear positive effect. Interventions with components involving the human factors of Education and Assessment, Dietary Recommendations, Exercise, and Rest and Relaxation increase the likelihood of not being readmitted to the hospital for heart failure.

Embodiments of a system herein can be configured to coordinate with an electronic medical records systems to identify any potential risk factors and possible interventions. Embodiments can identify measures to conduct data analysis and can conduct data analysis and data mining for specific queries, for example.

A decision support system for reducing/preventing readmission for heart failure patients can be utilized by a clinician. For example, a patient can visit a clinician, the clinician can input selections into a decision support system, perform readmission analysis and analyze results, and provide advice to patient to prevent or reduce readmission for heart failure.

Parameters (e.g., risk factors) used by one or more embodiments of a system in accordance with this disclosure that affect hospital re-admissions for cardiac diseases can include the following:

Choice—People who believe that they can control their own lives have a higher chance of becoming healthier.

Rest—Having a good sleep and relaxation reduces stress and blood pressure.

Environment—Improvement in external environment and surroundings helps with improving our health and reduce stress Trust—Trust, e.g., in a higher power such as God, can aid in reducing stress and faster healing.

Activity—Activity helps in physical and mental conditioning, the goal must be to be active in mind, body, and spirit.

Interpersonal Relationships—Having a strong interpersonal relationship helps in improving health. This also involves having good faith in the physician.

Outlook—Our mind influences our body and our attitude impacts our health.

Nutrition—Nutrition is the fuel that drives the whole body. Small improvements in nutrition can have a huge effect on overall health.

Home Visits—Involves either a doctor, nurse, or other clinician visiting the patient at home.

Tech—Intervention using telehealth, remote monitoring systems, patient education portals, and other forms of information technology.

These parameters can each include a corresponding intervention as appreciated by those having ordinary skill in the art in view of this disclosure. Also, this list is non-limiting and any other suitable parameters are contemplated herein.

In accordance with the above, referring to FIG. 1, a method 100 of treating a patient to prevent heart failure readmission can include identifying (e.g., at block 101) one or more risk factors for the patient (e.g., by determining the habits of the patient, and/or the psychological state of the patient). The method can include selecting (e.g., at block 103) one or more interventions relating to the one or more risk factors in a graphical user interface (GUI) of a treatment support system.

The method also includes receiving (e.g., at block 105, on the GUI) a statistical score of the one or more interventions to determine the effect of the one or more selected interventions on heart failure readmission. The method can also include treating (e.g., at block 107) the patient as a function of the received statistical score using the one or more interventions.

The one or more interventions can include at least one of rest intervention, environment intervention, nutrition intervention, activity intervention, home visit intervention, technology intervention, interpersonal relationship intervention, or patient psychological intervention, or any combination thereof. For example, the clinician can prescribe a particular diet, recurring activity, and/or behavior change for example.

Patient psychological intervention can include at least one of patient choice intervention, trust (e.g., faith) intervention, or patient outlook intervention, or any combination thereof. For example, the clinician can prescribe positive thinking and control of thought, and/or avoidance of negative relationships with others, e.g., in addition to a particular nutrition intervention and activity intervention.

Receiving the statistical score can include receiving at least one of a significance value, a beta value, or odds ratio of avoiding readmission compared to treatment without the one or more interventions. In certain embodiments, all of the above can be received simultaneously.

Figure 2:
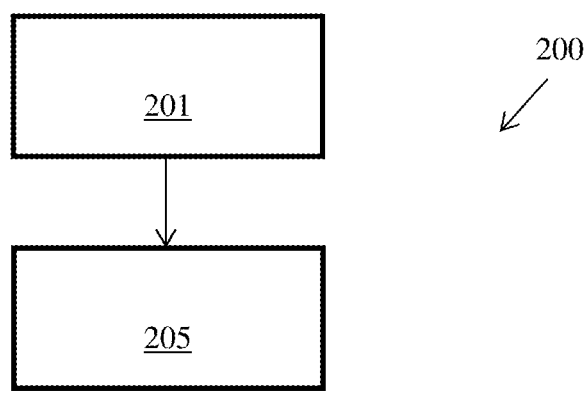
FIG. 2 is a schematic diagram of an embodiment of a system in accordance with this disclosure.
Figure 3A:
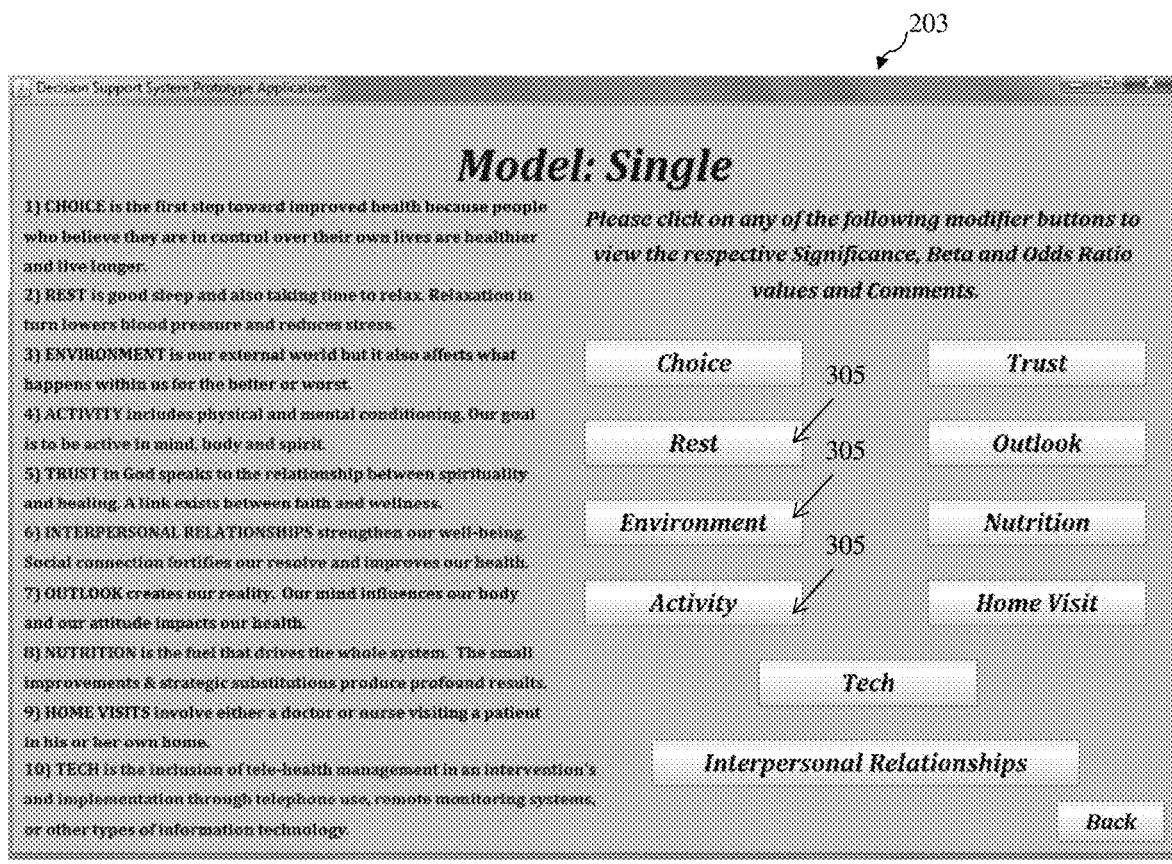
FIG. 3A illustrates an embodiment of a graphical user interface (GUI) in accordance with this disclosure, showing a single intervention model pane.
Figure 3B:
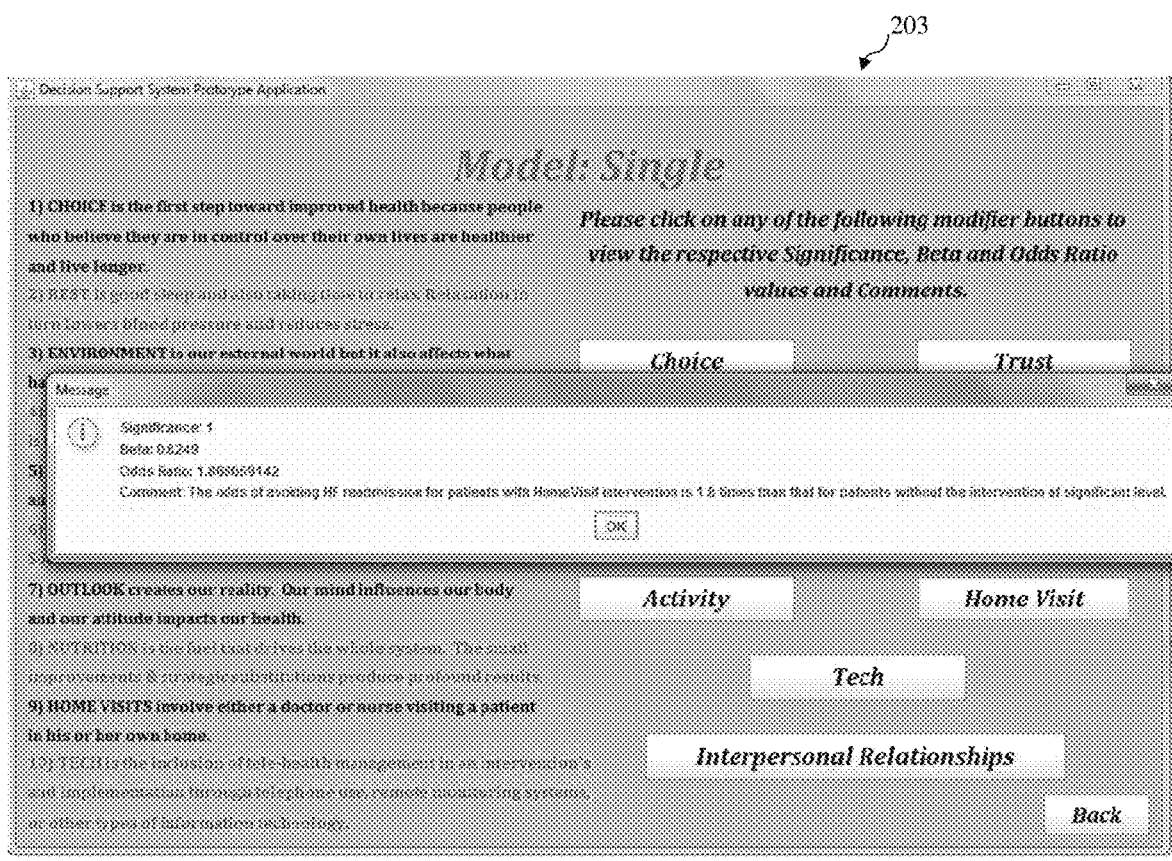
FIG. 3B illustrates an embodiment of a graphical user interface (GUI) in accordance with this disclosure, showing a statistical score being displayed for a first selected intervention.
Figure 3C:
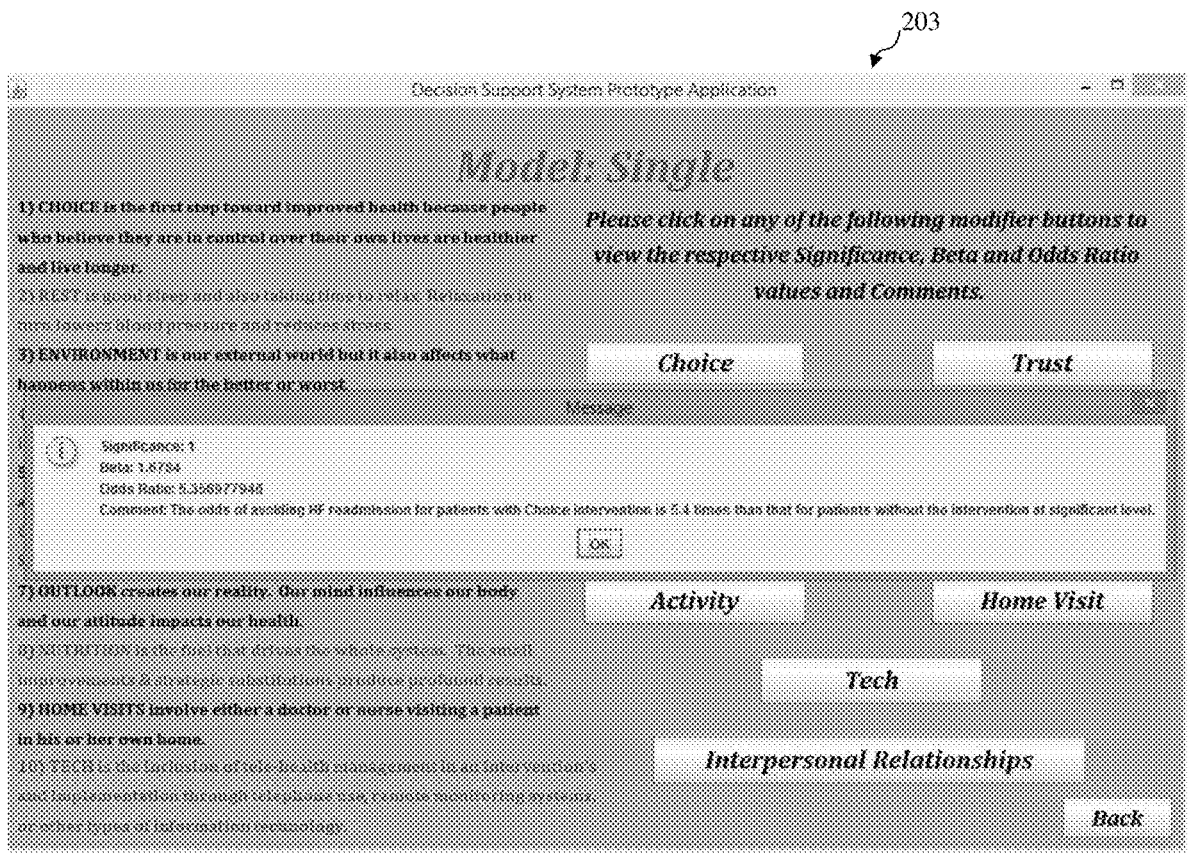
FIG. 3C illustrates an embodiment of a graphical user interface (GUI) in accordance with this disclosure, showing a statistical score being displayed for a second selected intervention.
Figure 3D:
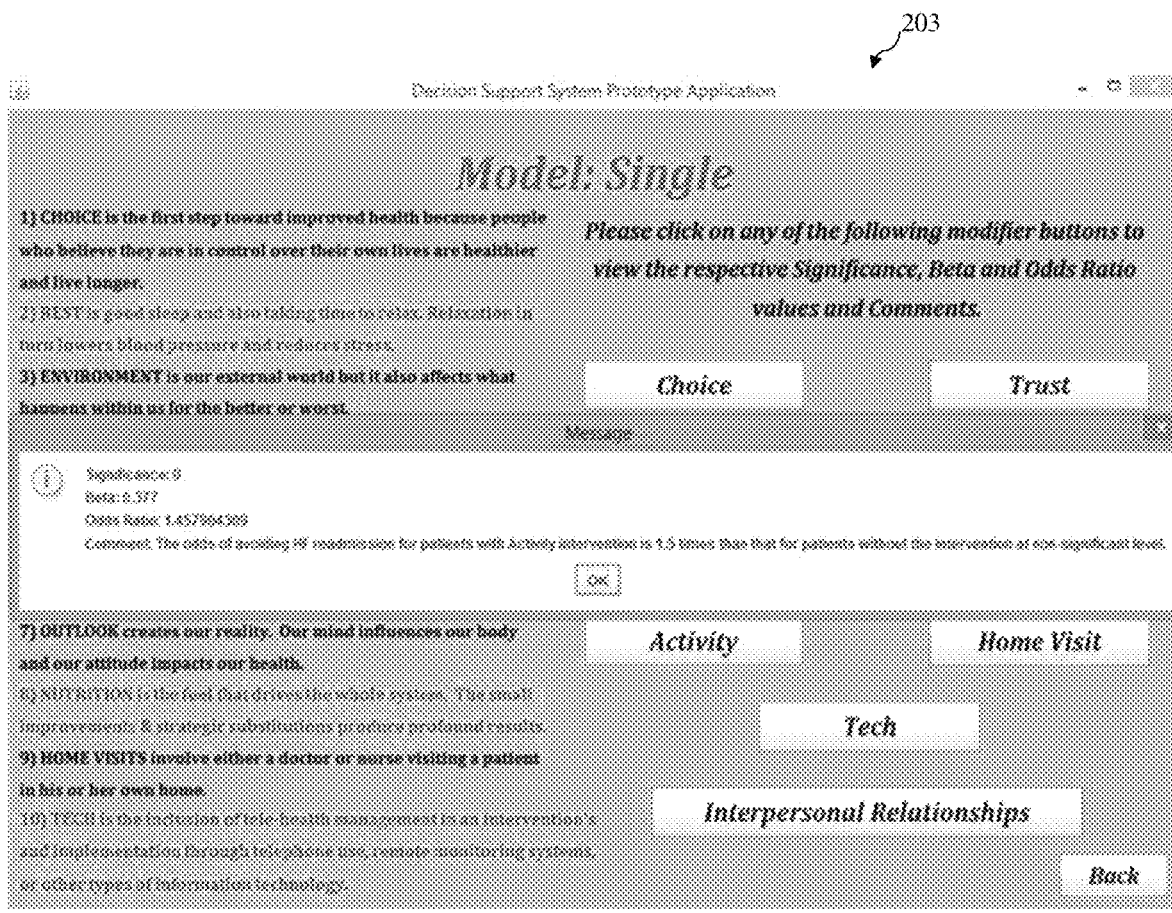
FIG. 3D illustrates an embodiment of a graphical user interface (GUI) in accordance with this disclosure, showing a statistical score being displayed for a third selected intervention.
Figure 3E:
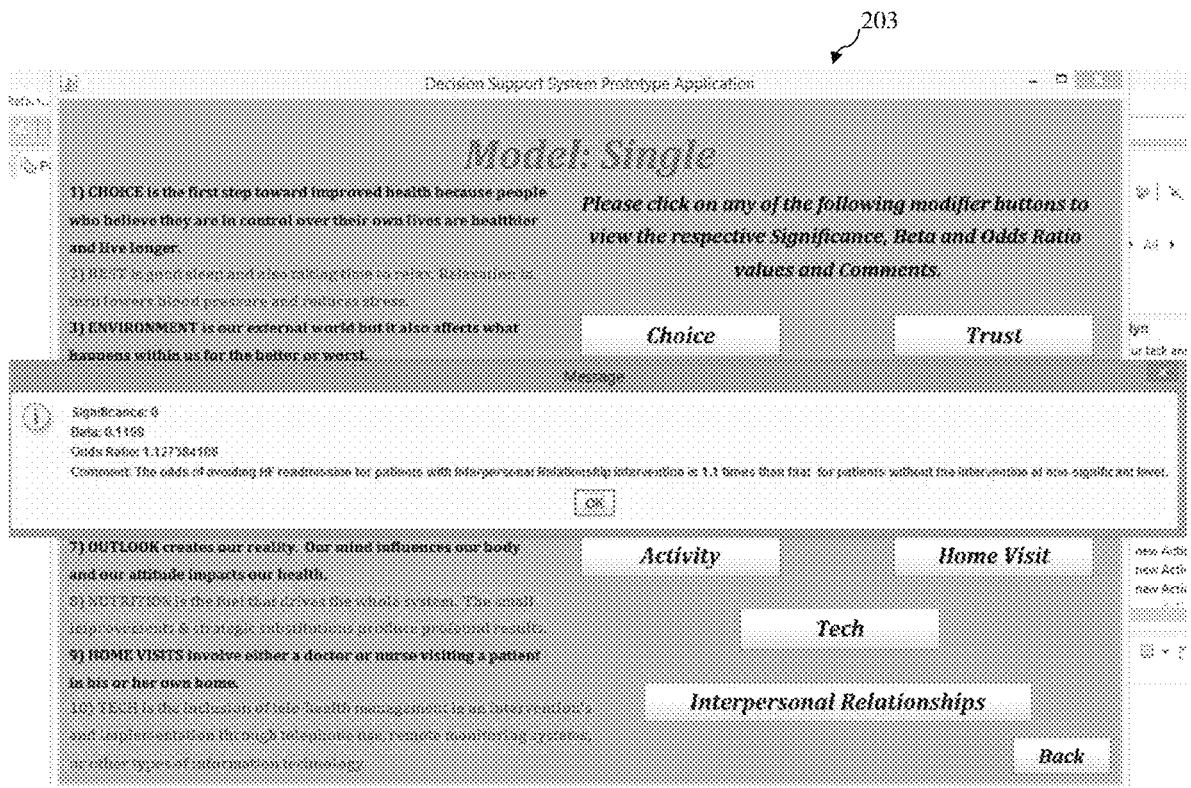
FIG. 3E illustrates an embodiment of a graphical user interface (GUI) in accordance with this disclosure, showing a statistical score being displayed for a fourth selected intervention.
Figure 3F:
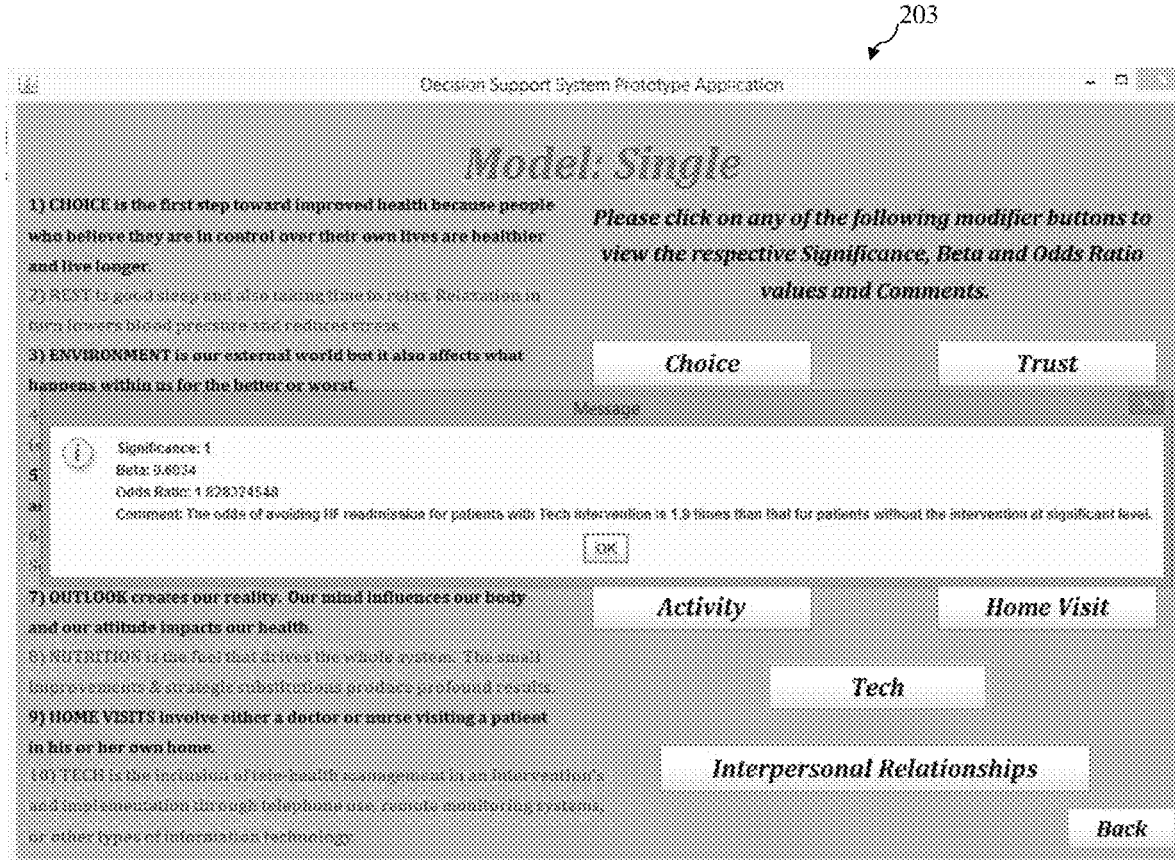
FIG. 3F illustrates an embodiment of a graphical user interface (GUI) in accordance with this disclosure, showing a statistical score being displayed for a fifth selected intervention.
Figure 4A:
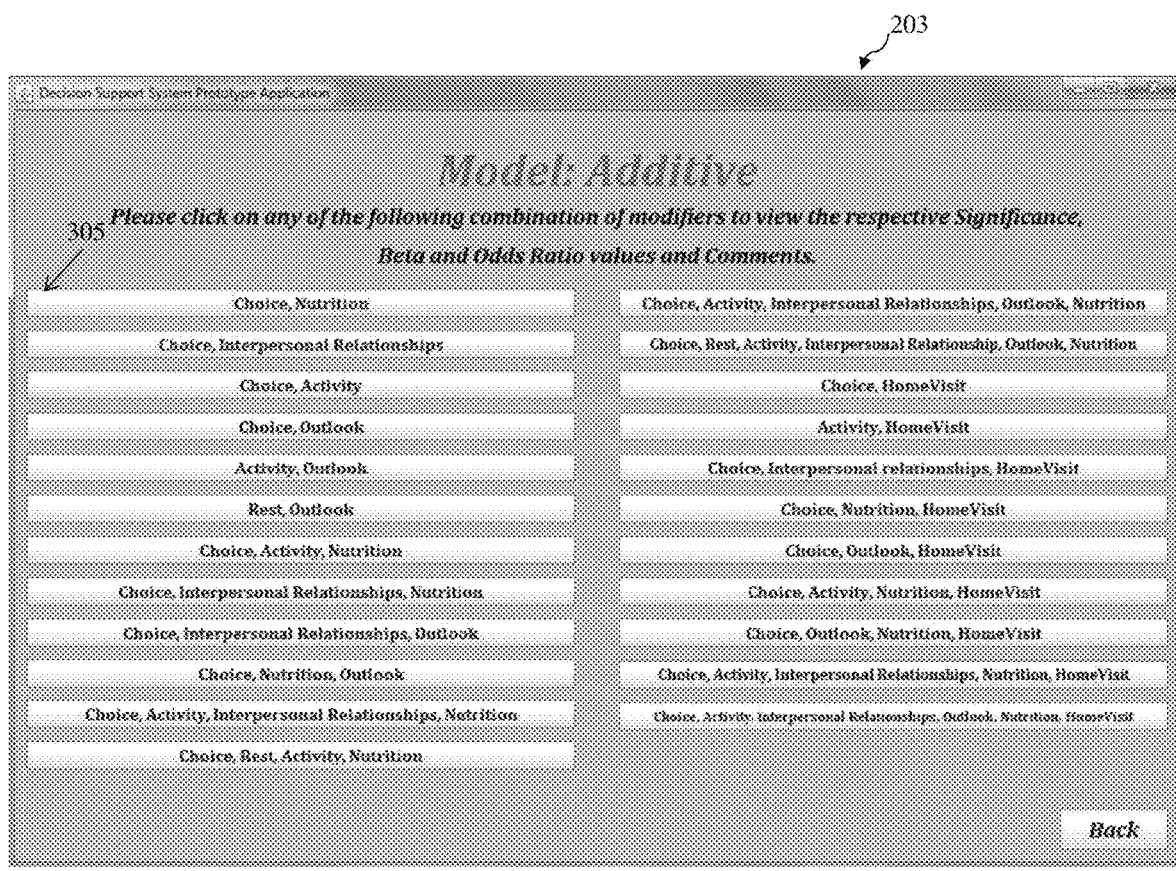
FIG. 4A illustrates an embodiment of a graphical user interface (GUI) in accordance with this disclosure, showing an additive intervention model pane.

In accordance with at least one aspect of this disclosure, referring to FIG. 2, a treatment support system 200 for preventing readmission due to heart failure can include a database 201 comprising a plurality of readmission prevention statistical scores for a plurality of interventions and/or one or more combinations thereof. The system 200 can include a graphical user interface (GUI) 205 operatively connected to the database. Referring additionally to FIGS. 3A-4B, the GUI 203 can include a plurality of intervention buttons 305 which each display a corresponding intervention or combination of interventions (e.g., as shown in FIGS. 3A and 4A, respectively). The intervention buttons 305 can be configured to allow a clinician to select one or more interventions by clicking the one or more intervention buttons 305. As shown in FIGS. 3B-3F and FIG. 4B, for example, the GUI 203 can be configured to display a statistical score for the selected one or more interventions to allow the clinician to treat a patient as a function of the provided statistical score.

As described above with respect to certain embodiments of a method of treatment, the one or more interventions can include at least one of rest intervention, environment intervention, nutrition intervention, activity intervention, home visit intervention, technology intervention, interpersonal relationship intervention, or patient psychological intervention, or any combination thereof. In certain embodiments, patient psychological intervention includes at least one of patient choice intervention, trust intervention, or patient outlook intervention, or any combination thereof. Any suitable other alternative intervention types or combinations thereof are contemplated herein.

As shown, displaying the statistical score can include displaying (e.g., in a popup window or any other suitable location) at least one of a significance value, a beta value, or odds ratio of avoiding readmission compared to treatment without the one or more interventions. In certain embodiments, displaying the statistical score can include displaying all of the significance value, the beta value, and the odds ratio of avoiding readmission compared to treatment without the one or more interventions.

Figure 4B:
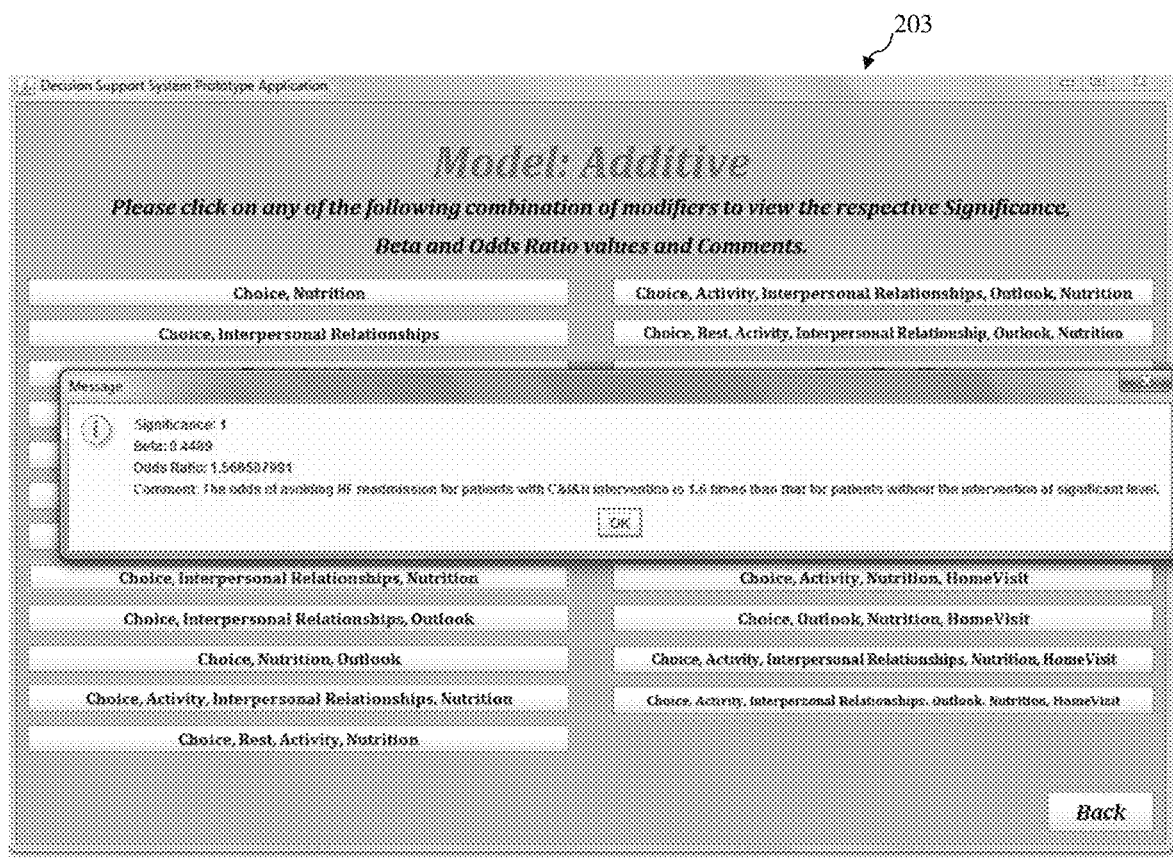
FIG. 4B illustrates an embodiment of a graphical user interface (GUI) in accordance with this disclosure, showing a statistical score being displayed for a first selected combination of interventions.

As shown in FIGS. 3A-3F, the GUI 203 can include a single intervention model pane which includes only single intervention buttons that each display a single intervention. Using such buttons 305 can cause the display of a statistical score of a single intervention that is selected. In certain embodiments, as shown in FIGS. 4A and 4B, the GUI 203 can additionally or alternatively include an additive intervention model pane which includes combination intervention buttons 305 that each display combination interventions. Using such buttons 305 can cause the display of a statistical score of a combination intervention that is selected.

As shown in FIG. 4A, in certain embodiments, the combination intervention buttons can include a Choice*Interpersonal Relationships*Nutrition button for displaying a statistical score from the database for the combination of patient choice intervention, interpersonal relationship intervention, and nutrition intervention. In certain embodiments, the combination intervention buttons can include a Choice*Outlook*Nutrition button for displaying a statistical score from the database for the combination of patient choice intervention, patient outlook intervention, and nutrition intervention.

In accordance with at least one aspect of this disclosure, a non-transitory computer readable medium includes computer readable instructions configured to cause a computer to perform a method. The method includes displaying a graphical user interface (GUI) including a plurality of intervention buttons which each display a corresponding intervention or combination of interventions, the intervention buttons configured to allow a clinician to select one or more interventions by clicking the one or more intervention buttons. The method also includes receiving a selection of an intervention button corresponding to the one or more interventions from the user (e.g., by the user clicking or otherwise selecting one of the intervention buttons).

The method can include looking up a statistical score in a database of the intervention or combination of interventions that corresponds to the selected intervention button, and displaying the statistical score in the GUI for the selected intervention or combination of interventions to allow the clinician to treat a patient as a function of the provided statistical score. The one or more interventions can be as described above, for example.

Displaying the statistical score can include displaying at least one of a significance value, a beta value, or odds ratio of avoiding readmission compared to treatment without the one or more interventions. In certain embodiments, displaying the statistical score includes displaying all of the significance value, the beta value, and the odds ratio of avoiding readmission compared to treatment without the one or more interventions.

Displaying the GUI can include displaying a single intervention model pane which includes only single intervention buttons that each display a single intervention, wherein displaying the statistical score includes displaying a statistical score of a single intervention that is selected. Displaying the GUI can include displaying an additive intervention model pane which includes combination intervention buttons that each display combination interventions, wherein displaying the statistical score includes displaying of a statistical score of a combination intervention that is selected. In certain embodiments, one or more single intervention buttons can be displayed in the same pane or screen as one or more combination intervention buttons such that there does not need to be a separate single intervention model pane from an additive intervention pane.

In certain embodiments, displaying the statistical score can include displaying a score window over the model pane of the GUI, or in any other suitable manner. It is contemplated that the statistical score can be displayed in any suitable location in the GUI (e.g., on the selected intervention button by changing the text displayed on the selected intervention button).

Certain embodiments allow physicians to understand the effects of multiple interventions together and to prescribe treatment accordingly. Using certain embodiments, patients can have their chances of readmission reduced significantly.

As will be appreciated by those skilled in the art, aspects of the present disclosure may be embodied as a system, method, or computer program product. Accordingly, aspects of this disclosure may take the form of an entirely hardware embodiment, an entirely software embodiment (including firmware, resident software, micro-code, etc.), or an embodiment combining software and hardware aspects, all possibilities of which may be referred to herein as a "circuit," "module," or "system." A "circuit," "module," or "system" can include one or more portions of one or more separate physical hardware and/or software components that can together perform the disclosed function of the "circuit," "module," or "system", or a "circuit," "module," or "system" can be a single self-contained unit (e.g., of hardware and/or software). Furthermore, aspects of this disclosure may take the form of a computer program product embodied in one or more computer readable medium(s) having computer readable program code embodied thereon.

Any combination of one or more computer readable medium(s) may be utilized. The computer readable medium may be a computer readable signal medium or a computer readable storage medium. A computer readable storage medium may be, for example, but not limited to, an electronic, magnetic, optical, electromagnetic, infrared, or semiconductor system, apparatus, or device, or any suitable combination of the foregoing. More specific examples (a non-exhaustive list) of the computer readable storage medium would include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a magnetic storage device, or any suitable combination of the foregoing. In the context of this document, a computer readable storage medium may be any tangible medium that can contain, or store a program for use by or in connection with an instruction execution system, apparatus, or device.

A computer readable signal medium may include a propagated data signal with computer readable program code embodied therein, for example, in baseband or as part of a carrier wave. Such a propagated signal may take any of a variety of forms, including, but not limited to, electromagnetic, optical, or any suitable combination thereof. A computer readable signal medium may be any computer readable medium that is not a computer readable storage medium and that can communicate, propagate, or transport a program for use by or in connection with an instruction execution system, apparatus, or device.

Program code embodied on a computer readable medium may be transmitted using any appropriate medium, including but not limited to wireless, wireline, optical fiber cable, RF, etc., or any suitable combination of the foregoing.

Computer program code for carrying out operations for aspects of this disclosure may be written in any combination of one or more programming languages, including an object oriented programming language such as Java, Smalltalk, C++ or the like and conventional procedural programming languages, such as the "C" programming language or similar programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider).

Aspects of the this disclosure may be described above with reference to flowchart illustrations and/or block diagrams of methods, apparatus (systems) and computer program products according to embodiments of this disclosure. It will be understood that each block of any flowchart illustrations and/or block diagrams, and combinations of blocks in any flowchart illustrations and/or block diagrams, can be implemented by computer program instructions. These computer program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in any flowchart and/or block diagram block or blocks.

These computer program instructions may also be stored in a computer readable medium that can direct a computer, other programmable data processing apparatus, or other devices to function in a particular manner, such that the instructions stored in the computer readable medium produce an article of manufacture including instructions which implement the function/act specified in the flowchart and/or block diagram block or blocks.

The computer program instructions may also be loaded onto a computer, other programmable data processing apparatus, or other devices to cause a series of operational steps to be performed on the computer, other programmable apparatus or other devices to produce a computer implemented process such that the instructions which execute on the computer or other programmable apparatus provide processes for implementing the functions/acts specified herein.

Any suitable combination(s) of any disclosed embodiments and/or any suitable portion(s) thereof are contemplated herein as appreciated by those having ordinary skill in the art.

Those having ordinary skill in the art understand that any numerical values disclosed herein can be exact values or can be values within a range. Further, any terms of approximation (e.g., "about", "approximately", "around") used in this disclosure can mean the stated value within a range. For example, in certain embodiments, the range can be within (plus or minus) 20%, or within 10%, or within 5%, or within 2%, or within any other suitable percentage or number as appreciated by those having ordinary skill in the art (e.g., for known tolerance limits or error ranges).

The embodiments of the present disclosure, as described above and shown in the drawings, provide for improvement in the art to which they pertain. While the subject disclosure includes reference to certain embodiments, those skilled in the art will readily appreciate that changes and/or modifications may be made thereto without departing from the spirit and scope of the subject disclosure.

What is claimed is:

1. A method of treating a patient to prevent heart failure readmission, comprising:
   identifying one or more risk factors for the patient associated with a plurality of latent variables in a database of latent variables;
   selecting one or more interventions relating to one or more of the plurality of latent variables in a graphical user interface of a treatment support system, wherein the latent variables include Choice, Rest, Environment, Activity, Trust, Interpersonal Relationship, Outlook, and Nutrition;
   receiving a statistical score of the one or more interventions to determine the effect of the one or more selected interventions on heart failure readmission as a function of the plurality of latent variables; and
   providing targeted treatment to a patient as a function of the received statistical score using the one or more interventions based upon the plurality of latent variables.

2. The method of claim 1, wherein the one or more interventions includes at least one of rest intervention, environment intervention, nutrition intervention, activity intervention, home visit intervention, technology intervention, interpersonal relationship intervention, or patient psychological intervention, or any combination thereof.

3. The method of claim 2, wherein patient psychological intervention includes at least one of patient choice intervention, trust intervention, or patient outlook intervention, or any combination thereof.

4. The method of claim 1, wherein receiving the statistical score includes receiving at least one of a significance value, a beta value, or odds ratio of avoiding readmission compared to treatment without the one or more interventions.

5. A treatment support system for preventing readmission due to heart failure, comprising:
   a database comprising a plurality of readmission prevention statistical scores for a plurality of latent variables and interventions associated with the plurality of latent variables and/or one or more combinations thereof, wherein the latent variables include Choice, Rest, Environment, Activity, Trust, Interpersonal Relationship, Outlook, and Nutrition, wherein the readmission prevention statistical scores are based on Chi-Squared Test Goodness of Fit;
   a graphical user interface (GUI) operatively connected to the database and including a plurality of intervention buttons which each display a corresponding intervention or combination of interventions, the plurality of intervention buttons configured to allow a clinician to select one or more interventions by clicking the one or more of the plurality of intervention buttons, wherein the GUI is configured to display a statistical score for the selected one or more interventions to allow the clinician to treat a patient as a function of the provided statistical score based on the Chi-Squared Test Goodness of Fit.

6. The system of claim 5, wherein the one or more interventions includes at least one of interpersonal relationship intervention or patient psychological intervention.

7. The system of claim 6, wherein patient psychological intervention includes at least one of patient choice intervention, trust intervention, or patient outlook intervention, or any combination thereof.

8. The system of claim 7, wherein displaying the statistical score includes displaying at least one of a significance value, a beta value, or odds ratio of avoiding readmission compared to treatment without the one or more interventions.

9. The system of claim 8, wherein displaying the statistical score includes displaying all of the significance value, the beta value, and the odds ratio of avoiding readmission compared to treatment without the one or more interventions.

10. The system of claim 8, wherein the GUI includes a single intervention model pane which includes only single intervention buttons that each display a single intervention and that cause the display of a statistical score of a single intervention that is selected.

11. The system of claim 10, wherein the GUI includes an additive intervention pane which includes combination intervention buttons that each display combination interventions and that cause the display of a statistical score of a combination intervention that is selected.

12. The system of claim 11, wherein the combination intervention buttons include a Choice*Interpersonal Relationships*Nutrition button for displaying a statistical score from the database for the combination of patient choice intervention, interpersonal relationship intervention, and nutrition intervention.

13. The system of claim 12, wherein the combination intervention buttons include a Choice*Outlook*Nutrition button for displaying a statistical score from the database for the combination of patient choice intervention, patient outlook intervention, and nutrition intervention.

14. A non-transitory computer readable medium, comprising computer readable instructions configured to cause a computer to perform a method, the method comprising:
displaying a graphical user interface (GUI) including a plurality of intervention buttons which each display a corresponding intervention or combination of interventions, the plurality of intervention buttons configured to allow a clinician to select one or more interventions by clicking one or more of the plurality of intervention buttons;
receiving a selection of an intervention button corresponding to the one or more interventions from the clinician;
looking up a statistical score in a database of statistical scores associated with a plurality of latent variables, wherein the latent variables include Choice, Rest, Environment, Activity, Trust, Interpersonal Relationship, Outlook, and Nutrition, based on Chi-Squared Test Goodness of Fit, of the intervention or combination of interventions that corresponds to the selected intervention button; and
displaying the statistical score in the GUI for the selected intervention or combination of interventions to allow the clinician to treat a patient as a function of the provided statistical score based on the latent variables.

15. The non-transitory computer readable medium of claim 14, wherein the one or more interventions includes at least one of interpersonal relationship intervention or patient psychological intervention.

16. The non-transitory computer readable medium of claim 15, wherein patient psychological intervention includes at least one of patient choice intervention, trust intervention, or patient outlook intervention, or any combination thereof.

17. The non-transitory computer readable medium of claim 16, wherein displaying the statistical score includes displaying at least one of a significance value, a beta value, or odds ratio of avoiding readmission compared to treatment without the one or more interventions.

18. The non-transitory computer readable medium of claim 17, wherein displaying the statistical score includes displaying all of the significance value, the beta value, and the odds ratio of avoiding readmission compared to treatment without the one or more interventions.

19. The non-transitory computer readable medium of claim 18, wherein displaying the GUI includes displaying a single intervention model pane which includes only single intervention buttons that each display a single intervention, wherein displaying the statistical score includes displaying a statistical score of a single intervention that is selected.

20. The non-transitory computer readable medium of claim 19, wherein displaying the GUI includes displaying an additive intervention model pane which includes combination intervention buttons that each display combination interventions, wherein displaying the statistical score includes displaying of a statistical score of a combination intervention that is selected.

* * * * *